(12) United States Patent
Perumal et al.

(10) Patent No.: US 8,140,166 B2
(45) Date of Patent: Mar. 20, 2012

(54) ACTIVATING A NON-ISOMETRIC FUNCTIONAL MOVEMENT THROUGH ELECTRICAL STIMULATION

(75) Inventors: Ramu Perumal, Newark, DE (US); Anthony S. Wexler, Davis, CA (US); Stuart Binder-Macleod, Newark, DE (US); Jun Ding, New Castle, DE (US)

(73) Assignee: The Regents of the University of California, Oakland, CA (US)

( * ) Notice: Subject to any disclaimer, the term of this patent is extended or adjusted under 35 U.S.C. 154(b) by 898 days.

(21) Appl. No.: 11/815,950

(22) PCT Filed: Feb. 10, 2006

(86) PCT No.: PCT/US2006/004969
§ 371 (c)(1),
(2), (4) Date: Aug. 4, 2008

(87) PCT Pub. No.: WO2006/086755
PCT Pub. Date: Aug. 17, 2006

(65) Prior Publication Data
US 2009/0012579 A1    Jan. 8, 2009

Related U.S. Application Data

(60) Provisional application No. 60/652,369, filed on Feb. 10, 2005.

(51) Int. Cl.
*A61N 1/18* (2006.01)
(52) U.S. Cl. .............. 607/49; 607/48; 607/77; 607/78
(58) Field of Classification Search .............. 607/48–49, 607/77–78; 600/546–547
See application file for complete search history.

(56) References Cited

U.S. PATENT DOCUMENTS
2004/0172097 A1 * 9/2004 Brodard et al. ................. 607/49
* cited by examiner

*Primary Examiner* — Niketa Patel
*Assistant Examiner* — Rex R Holmes
(74) *Attorney, Agent, or Firm* — Park, Vaughn, Fleming & Dowler LLP (57) ABSTRACT

A system that activates a muscle to produce a functional movement in a subject through electrical stimulation is described. During operation, the system first obtains a non-isometric model which defines a functional movement associated with the muscle in response to electrical stimulation of the muscle. Next, the system uses the non-isometric model to compute an electrical stimulation which produces a desired functional movement in the subject. The system then applies the computed electrical stimulation to the muscle to produce the desired functional movement in the subject.

30 Claims, 4 Drawing Sheets

ACTIVATING A NON-ISOMETRIC FUNCTIONAL MOVEMENT THROUGH ELECTRICAL STIMULATION

GOVERNMENT LICENSE RIGHTS

This invention was made with United States Government support under Contract No. HD-36797 awarded by the National Institutes of Health. The United States Government has certain rights in the invention.

BACKGROUND

1. Field of the Invention

The present invention relates to using functional electrical stimulation to artificially activate muscle movement. More specifically, the present invention relates to a method and apparatus for activating a muscle to produce a non-isometric functional movement in a body part through functional electrical stimulation.

2. Related Art

Functional electrical stimulation (FES) of skeletal muscles can restore functional movements, such as standing or walking in patients with upper motor neuron lesions. This is achieved by applying the FES to paralyzed or weak muscles in the patients to artificially activate the functional movements.

Unfortunately, despite many technical advances, the FES has not had desirable impact on rehabilitation. This lack of effectiveness in practice is caused by several factors. Firstly, the physiological and biomechanical processes involved in the generation of FES-elicited movements are highly nonlinear and time varying. Hence, numerous tests would be required to find the desired stimulation patterns necessary to produce the desired muscle force and limb motion for each patient and for each functional movement. Secondly, commercially available FES systems are typically open-loop systems which make controlling the movements of paralyzed limbs in patients extremely difficult. Finally, other factors that occur during a FES-elicited movement, such as muscle fatigue, spasticity, and the influence of voluntary upper-body forces further complicate the control task.

One solution that can partially overcome the above-described shortcomings is the use of mathematical muscle models in conjunction with FES systems that monitor muscle performance. Mathematical models that are accurate and predictive enable FES stimulators to deliver patterns customized for each person to perform a desired functional movement while continuously adapting the stimulation protocols to the actual needs of the patient.

Previously, phenomenological Hill-type, Huxley-type cross-bridge, or analytical approaches have been developed to model the behavior of muscle contraction under both isometric and non-isometric conditions. Unfortunately, all of the above mathematical models that have been developed to date have one or all of the following drawbacks: (1) they are applicable only to isometric conditions—it is desirable to extend the models to predict non-isometric contractions when the limbs are allowed to move freely in response to the FES; (2) they are only able to predict muscle forces and associated movements in response to a narrow range of stimulation frequencies—it is desirable to develop models that are able to predict muscle forces and movements to a wide range of stimulation patterns and physiological conditions; and (3) too many model parameters need to be identified, which makes the real-time implementation of the FES-based system impossible—it is desirable to minimize the number of model parameters and still be able to capture the behavior of the muscle in response to the FES.

Hence, what is needed is a method and an apparatus that uses a mathematical model which is capable of predicting a desired FES to activate a muscle to produce a desired non-isometric movement without the above-described problems.

SUMMARY

One embodiment of the present invention provides a system that activates a muscle to produce a functional movement in a subject through electrical stimulation. During operation, the system first obtains a non-isometric model which defines a functional movement associated with the muscle in response to electrical stimulation of the muscle. Next, the system uses the non-isometric model to compute an electrical stimulation which produces a desired functional movement in the subject. The system then applies the computed electrical stimulation to the muscle to produce the desired functional movement in the subject.

In a variation on this embodiment, the system obtains the non-isometric model by determining parameters for the non-isometric model empirically for the subject.

In a further variation on this embodiment, the system determines parameters for the non-isometric model by: (1) determining a first set of parameters under isometric conditions; (2) determining a second set of parameters under isovelocity conditions; and (3) determining a third set of parameters under non-isometric conditions.

In a variation on this embodiment, the non-isometric model defines the relationship between force behaviors in response to an electrical stimulation and movements in response to the electrical stimulation.

In a further variation on this embodiment, the force behaviors include: the force generated by non-isometric contraction of the muscle; and the time derivative of the force generated by non-isometric contraction of the muscle.

In a further variation on this embodiment, the movements can include: (1) an angular displacement; (2) an angular velocity; and (3) an angular acceleration.

In a variation on this embodiment, an electrical stimulation is a train of pulses, wherein the train of pulses is characterized by: (1) interpulse interval (IPI); (2) duration of the pulses; and (3) amplitude of the pulses.

In a further variation on this embodiment, the electrical stimulation can comprise: a constant IPI within the train of pulses; or a variable IPI within the train of pulses.

In a further variation on this embodiment, after applying the computed electrical stimulation to the muscle, the system next measures a functional movement in the subject in response to the computed electrical stimulation. Next, the system computes a difference between the measured functional movement and the desired functional movement. The system then uses the computed difference as feedback to adjust the electrical stimulation to facilitate obtaining the desired functional movement in the subject. Finally, the system applies the adjusted electrical stimulation to the muscle.

In a further variation on this embodiment, the system adjusts the electrical stimulation by changing one of the following: (1) the IPI; (2) the duration of the pulses; or (3) the amplitude of the pulses.

In a variation on this embodiment, the system computes the electrical stimulation by computing an electrical stimulation that substantially minimizes fatigue in the muscle while producing the desired functional movement in the subject.

BRIEF DESCRIPTION OF THE FIGURES

Table 1 presents a list of detailed definitions of the symbols used in the mathematical model for the non-isometric movement.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the claims.

The data structures and code described in this detailed description are typically stored on a computer-readable storage medium, which may be any device or medium that can store code and/or data for use by a computer system. This includes, but is not limited to, magnetic and optical storage devices such as disk drives, magnetic tape, CDs (compact discs), DVDs (digital versatile discs or digital video discs), or any device capable of storing data usable by a computer system.

Mathematical Model for Non-Isometric Movement

The model that describes a functional movement associated with the muscle in response to an electrical stimulation is summarized by a set of differential equations.

Before describing each of the differential equations in details, we first introduce "$Ca^{2+}$-troponin complex". The $Ca^{2+}$-troponin complex forms within the muscle when the muscle is stimulated by the FES, which causes the muscle to contract. In a preferred embodiment of the present invention, the FES is a train of pulses. During the initial phase of the FES, as the number of $Ca^{2+}$-troponin complexes increases in the muscle, the contraction force increases as well. We use a variable $C_N$ to represent the normalized concentration of $Ca^{2+}$-troponin complex in the stimulated muscle, and our first equation defines the dynamics of the rate-limiting step leading to the formation of the $Ca^{2+}$-troponin complex:

$$\dot{C}_N = \frac{1}{\tau_c} \sum_{i=1}^{n} R_i \exp\left(-\frac{t-t_i}{\tau_c}\right) - \frac{C_N}{\tau_c}, \quad (1)$$

wherein $\dot{C}_N$ is a shorthand for the time derivative of $C_N$. Note that Eq. (1) is a response to the train of pulses, wherein the summation is performed over n pulses delivered at time $t_i$ within the train of pulses until time t.

Some of the parameters of Eq. (1) are defined below and again summarized in Table 1, which presents a list of detailed definitions of the symbols used in the mathematical model:

t: Time since the beginning of the electrical stimulation;
$t_i$: Time when the ith pulse is delivered;
$\tau_c$: Time constant controlling the rise and decay of $C_N$;
$R_i$: Scaling term that accounts for the differences in the degree of activation produced by each pulse relative to the first pulse of the train.

Note that $R_i=1$ for i=1, and $R_i=1+(R_0-1)\exp[-(t_i-t_{i-1})/\tau_c]$ for i>1, wherein $R_0$ is a mathematical term characterizing the magnitude of enhancement in $C_N$ due to the following stimulations. Note that when the stimulation stops, $C_N$ will begin an exponential decay governed by the term $-C_N/\tau_c$.

The second and the core equation is the force equation:

$$\dot{F} = \underbrace{[G(\theta)\dot{\theta} + A(\theta)]\frac{C_N}{K_M + C_N}}_{I} - \underbrace{\frac{F}{\tau_1 + \tau_2 \frac{C_N}{K_M + C_N}}}_{II}. \quad (2)$$

Eq. (2) represents the rate of change of the muscle force F due to the FES, wherein $\dot{F}$ is used as a shorthand for the time derivative of the muscle force F. The equation is derived from modeling the muscle as a linear spring, damper, and motor in series (see Wexler, A. S., Ding, J., Binder-Macleod, S. A., "A mathematical model that predicts skeletal muscle force," IEEE Transactions on Bio-Medical Engineering 44: 337-348, 1997). Note that the equation contains two terms: term I and II.

Term I represents force increase with time due to the FES. This increase in force F is driven by $C_N/(K_M+C_N)$ and is scaled by $A(\theta)$ and $G(\theta)\dot{\theta}$. Note that $C_N/(K_M+C_N)$ follows "Michaelis-Menton Kinetics" so that its value increases with the number of $Ca^{2+}$-troponin complex $C_N$. As a result, force F increases initially with increasing $C_N$. However, the force increase slows down and eventually saturates when $C_N \gg K_M$. $K_M$ is called the sensitivity of strongly bound cross-bridges to $C_N$, and is alternatively defined as the value of $C_N$ that achieves the half maximum of the force increase rate.

$A(\theta)$ is a variable that measures the strength of the muscle and a function of movement $\theta$ due to the force F. In one embodiment of the present invention, the movement is generated by the FES to quadriceps femoris muscle, which causes flexion of the knee which is measured by knee flexion angle $\theta$. In one embodiment of the present invention, $A(\theta)$ can be represented by:

$$A(\theta) = a(40-\theta)^2 + b(40-\theta) + A_{40}, \quad (2a)$$

where a, b and $A_{40}$ are all scaling factors that are defined in Table 1. Note that the movement due to the stimulated muscle force is not limited to angular movement of a joint. For example, the movement can also include the movement generated by linear contraction of the muscle.

$\dot{\theta}$ represents the angular velocity of a joint or linear velocity of the muscle while $G(\theta)$ is a factor that measures the strength decrease with increased velocity, and is a function of the movement $\theta$. In one embodiment of the present invention, $G(\theta)$ can be expressed as:

$$G(\theta)=V_1\theta \exp([3.0523/\tau_2-0.0574]\theta), \qquad (2b)$$

wherein $V_1$ is an empirically determined scaling factor, and $\tau_2$ represents a time constant of the force decay due to the extra friction between actin and myosin resulting from the presence of strongly bound cross-bridges in the muscle.

Term II in Eq. (2) represents the force decay due to two friction mechanisms in the muscle. The two friction mechanisms are characterized by $\tau_1$ and $\tau_2$ respectively, wherein $\tau_1$ is the time constant of force decay due to friction in the absence of $C_N$, i.e., no strongly bound cross-bridges in the muscle, and $\tau_2$ is the time constant of force decay due to friction in the presence of strongly bound cross-bridges in the muscle.

Note that in comparison to Hill-type models (see Perumal, R., Wexler, A. S., Ding, J., and Binder-Macleod, S. A., "Modeling the length dependence of isometric force in human quadriceps muscles," Journal of Biomechanics 35, 919-930, 2002), the force model of Eq. (2) has made the following improvements: (a) it takes into account the viscous resistance of the contractile and connective tissue in addition to the contractile and elastic component of the standard Hill model; (b) it models the rate of change of force with time rather than the force alone; and (c) the force-velocity relationship (modeled through the term $G(\theta)\dot{\theta}$) arises as a consequence of the model. In contrast, for Hill-type models the force-velocity relationship is introduced as part of the contractile element.

In the third and the last of the set of differential equations, we represents the general non-isometric movements for the lower leg in response to the electrical stimulation as:

$$\ddot{\theta} = \frac{L}{I}[(F_{LOAD} + F_M)\cos(\theta + \lambda) - F], \qquad (3)$$

wherein the parameters L, I, $F_{LOAD}$, $F_M$, and $\lambda$ are defined in Table 1. Note that Eq. (3) is specific to an angular movement due to knee flexion where L is the effective moment arm from the knee joint center of rotation to a point on the shank where all the forces are assumed to act. $\lambda$ is the resting angle that accounts for the difference between the knee flexion angle, $\theta$, when the leg is in a resting position at the beginning of the stimulation and the vertical angle of 90°. Hence, at the resting position, $\lambda+\theta$ will have a value of 90° which ensures that $(F_{load}+F_M)\cos(\theta+\lambda)$ will be zero at the beginning of the stimulation. We will discuss all the terms Eq. (3) in more detail below.

The model represented by Eqs. (1)-(3) is governed by 13 parameters: $R_0$, $\tau_c$, a, b, $A_{40}$, $\tau_1$, $\tau_2$, $K_M$, $V_1$, $F_{M-Isovel}$, L/I, $F_M$, and $\lambda$, wherein $R_0$ and $\tau_c$ are constants and the remaining parameters need to be determined for each subject individually. Note that parameter $F_{M-Isovel}$ is the value of parameter $F_M$ when the stimulated movement has a constant velocity, which is referred to as an "isovelocity condition."

Pulse Train

In one embodiment of the present invention, trains of pulses (or pulse trains) are used as standard FES to activate the muscle force and movement. In a preferred embodiment, the pulses are narrow square pulses, for example, pulses generated with transistor-transistor logic (TTL), and subsequently amplified to a specified voltage suitable for stimulating a subject's muscle. Each pulse train is identified by three variables: (1) interpulse intervals (IPIs): the time separation between adjacent pulses; (2) duration (i.e., width) of the pulses; and (3) amplitude of the pulses (in Volts).

(1) CFT

Figures 1A, 1B:
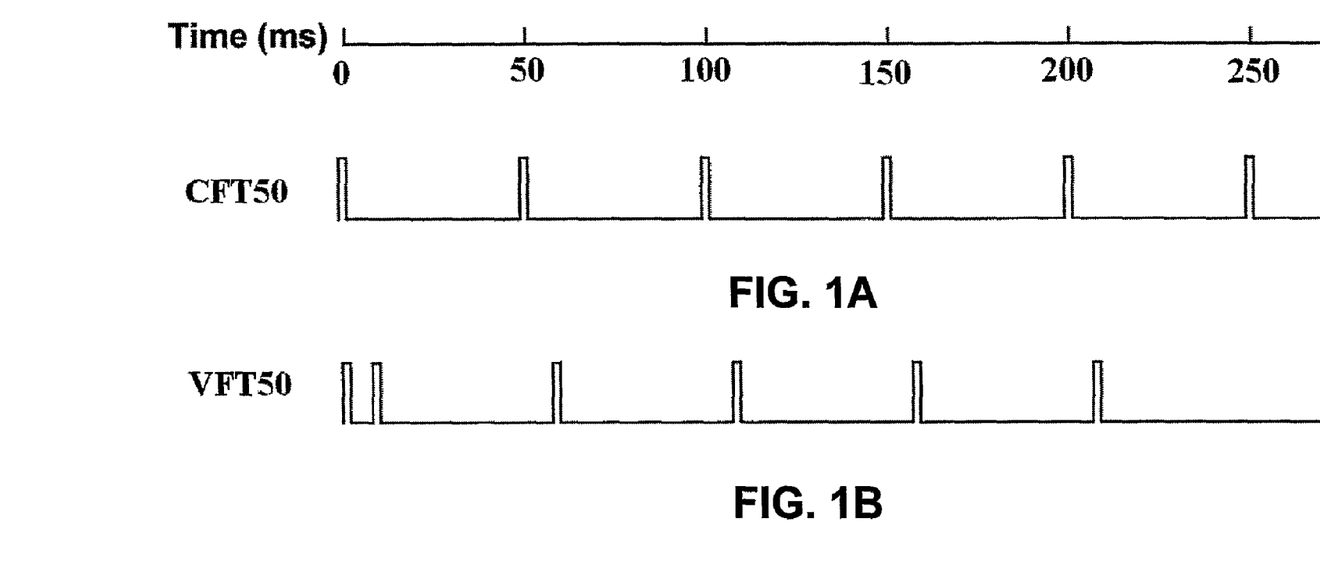
FIG. 1A illustrates an exemplary constant frequency train (CFT) with a 50 ms interpulse interval (IPI) and a constant pulse width in accordance with an embodiment of the present invention.
FIG. 1B illustrates an exemplary variable frequency train (VFT) with an initial IPI of 5 ms and the remaining IPIs of 80 ms in accordance with an embodiment of the present invention.

Traditionally, muscles are activated with constant frequency trains (CFTs), wherein the pulses within each train are separated by a constant IPI. FIG. 1A illustrates an exemplary CFT with a 50 ms IPI and a constant pulse width in accordance with an embodiment of the present invention. We refer to this CFT as CFT50 wherein 50 represents the 50 ms IPI. The same convention is applicable to CFTs with different IPIs. Furthermore, we refer to CFTs with different IPIs as having different stimulation frequencies. For example, CFT50 has a lower stimulation frequency than CFT30 (30 ms IPI) due to the longer IPI of the former.

(2) VFT

Studies have shown that varying the stimulation frequency and pattern within a pulse train can significantly affect the force generation from the muscle, as well as other factors associated with muscle performance, such as fatigue and spasticity. Hence, stimulation patterns for optimally maintaining a desired force or motion profile repetitively during the FES is more complex than CFTs. In one embodiment of the present invention, we use "variable frequency trains" (VFTs). FIG. 1B illustrates an exemplary VFT with an initial IPI of 5 ms and the remaining IPIs of 80 ms in accordance with an embodiment of the present invention. We refer to this VFT as VFT80 wherein 80 represents the 80 ms IPI of the second IPI in the train. The same convention is applicable to VFTs with the same initial IPI but different second IPIs.

(3) DFT

Figure 1C:
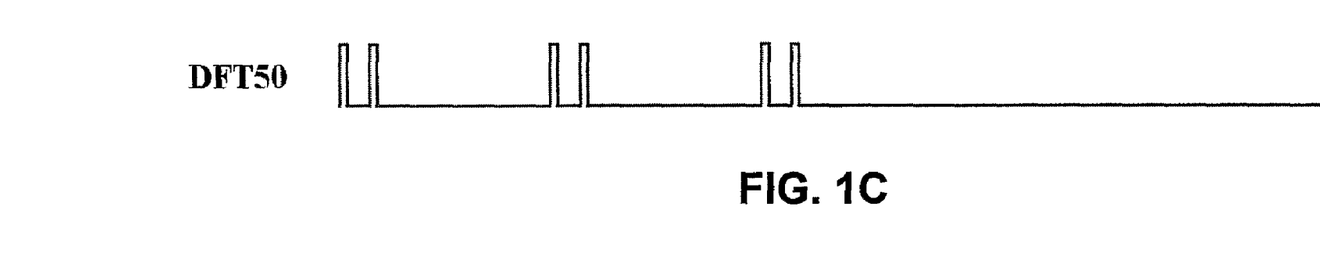
FIG. 1C illustrates an exemplary doublet frequency train (DFT) with 5 ms IPI doublets and 50 ms IPI between adjacent doublets in accordance with an embodiment of the present invention.

Another form of preferred pulse trains is referred to as "doublet frequency trains" (DFTs) wherein each DFT comprises pulse doublets throughout the train. FIG. 1C illustrates an exemplary DFT with 5 ms IPI doublets and 50 ms IPI between adjacent doublets in accordance with an embodiment of the present invention. We refer to this DFT as DFT50 wherein 50 represents the 50 ms IPI between adjacent doublets in the train. The same convention is applicable to DFTs with different in-between doublets IPIs.

Note that the types of pulse trains that may activate a desired functional movement are not limited to the three types mentioned above.

Determining Parameters in the Model Through Experiments (A) Experimental Setup

In one embodiment of the present invention, isometric force data, isovelocity force data, and general non-isometric force data are measured from the human quadriceps femoris muscle in response to the FES, which produces knee flexion movements in the lower leg.

Figure 2A:
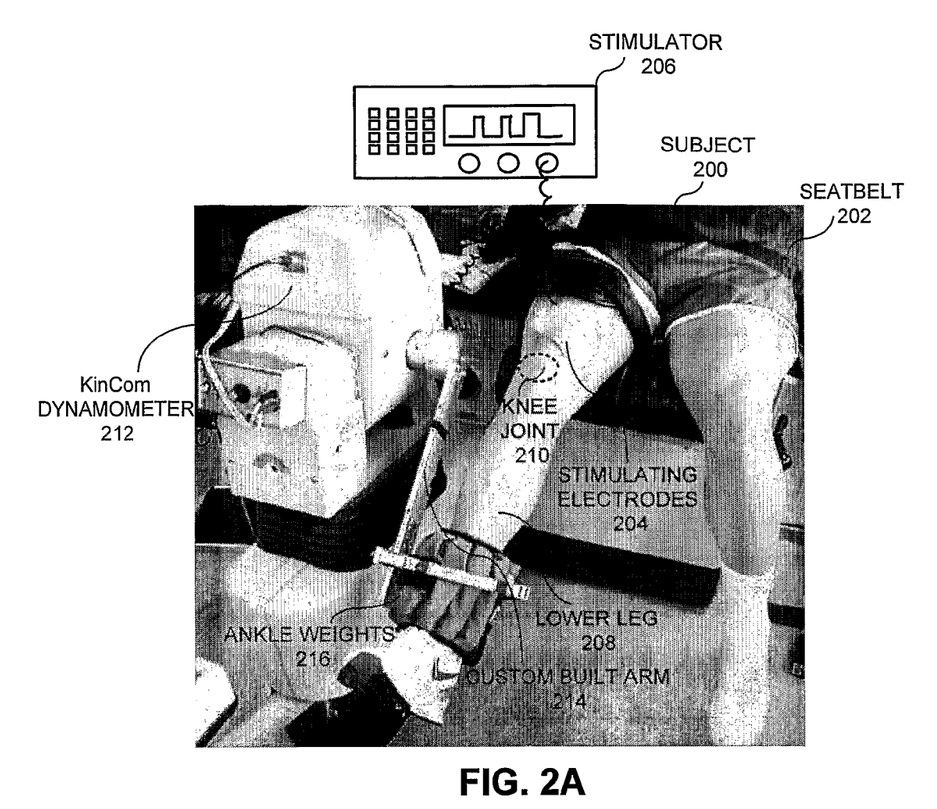
FIG. 2A illustrates a subject positioned in an experimental setup to measure lower leg movements in response to electrical stimulation in accordance with an embodiment of the present invention.

FIG. 2A illustrates a subject positioned in an experimental setup to measure lower leg movements in response to electrical stimulation in accordance with an embodiment of the present invention.

In FIG. 2A, subject 200 is affixed to a chair in a sitting position using a seatbelt 202. FES is applied through the electrodes 204 placed on the quadriceps femoris muscle, wherein the FES is generated and provided by an external stimulator 206. The FES causes lower leg 208 to move freely in a "swing" motion around knee joint 210. For the isometric and isovelocity movements of lower leg 208, force and angle data are measured using a KinCom dynamometer 212 (Chattecx Corp, Hixson, Tenn.) around the ankle joint of lower leg 208. In contrast, for the general non-isometric movements, a custom built arm 214 is mounted onto the shaft of KinCom dynamometer 212 through ball bearings. Hence, custom built arm 214 can rotate with minimum resistance to the movement about the knee joint center of rotation. To measure the rotation angle, custom built arm 214 contains a potentiometer, whose shaft is aligned with the knee joint center of rotation of subject 200. The distal end of custom built arm. 212 is attached above subject 200's ankle and hence the potentiometer measures the knee joint rotation angle during non-isometric contractions. Note that ankle weights 216 are placed just above the ankle joint. In response to the FES, the muscle contracts and causes lower leg 208 with ankle weights 216 to extend.

Figure 2B:
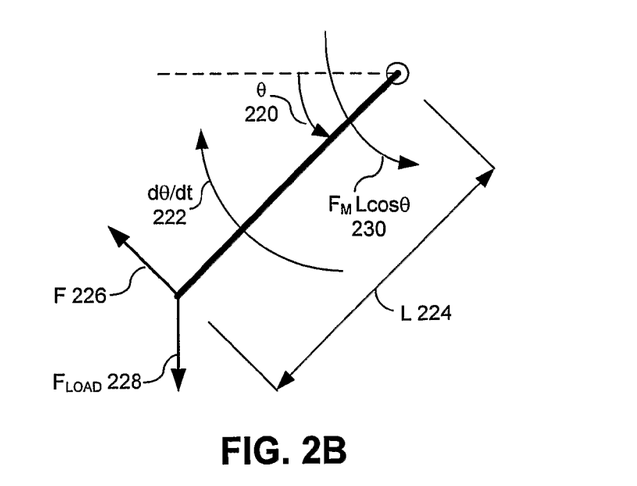
FIG. 2B illustrates a schematic representation of the lower leg modeled as a rigid body segment (tibia) when subjected to a stimulation in accordance with an embodiment of the present invention.

FIG. 2B illustrates a schematic representation of the lower leg modeled as a rigid body segment (tibia) when subjected to a stimulation in accordance with an embodiment of the present invention.

In FIG. 2B, θ (220) represents the knee flexion angle; $\dot{\theta}$ (i.e. dθ/dt) (222) represents the angular velocity; L (224) represents effective moment arm; F (226) represents the force due to the FES; $F_{LOAD}$ (228) represents the force due to ankle weights 216; and $F_M L \cos \theta$ (230) represents the resistance moment to knee extension due to passive elasticity of the knee joint and the weight of the lower leg, which is the weight of the shank and foot. F (226) is illustrated as a tangential force at the ankle joint because: (a) for isometric and isovelocity experimental setups, the force due to the FES is measured by a tangential uniaxial force transducer placed at the ankle joint and (b) for general non-isometric experimental setup, F (226) at the ankle joint is the force that that causes custom built arm 214 to rotate about the knee joint center.

For each subject, all data are measured in a single testing session. Each testing session includes three parts. First, subjects are tested under isometric conditions at knee flexion angles of 15°, 40°, 65°, and 90°. The testing order for each angle is randomly determined and a rest period of five minutes is provided between the angles. Next, subjects are tested at an isovelocity speed of –200°/s, wherein the negative sign is due to a constant "shortening velocity". Finally, non-isometric tests are performed with ankle weights of 0, 4.54 kg, and 9.08 kg. Again, the testing order for the non-isometric loads is randomly determined for each subject and a rest period of five minute is provided between testing each load. After testing is completed, the data from isometric, isovelocity, and general non-isometric testing are used to determine the parameters of the model. Furthermore, additional data are measured during the general non-isometric testing which are used to evaluate the predictive ability of the model.

(B) Determining Parameters in the Model

The parameters in the model are determined empirically using the above-described experimental setup for each subject under text. Specifically, the parameters are determined under one of the three conditions: (1) parameters a, b, $A_{40}$, $\tau_1$, $\tau_2$ and $K_M$ are determined under isometric conditions; (2) parameters $V_1$ and $F_{M\_Isovel}$ are determined under isovelocity conditions; and (3) parameters L/I, $F_M$, and λ are determined under general non-isometric conditions.

Figure 3:
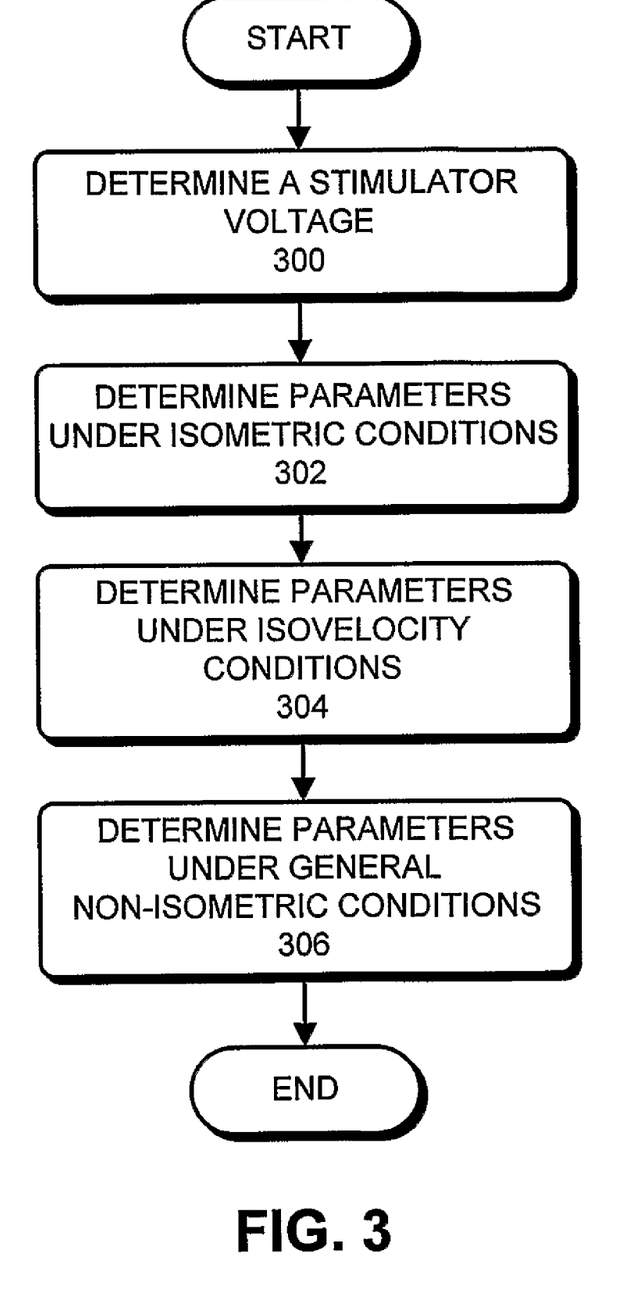
FIG. 3 presents a flowchart illustrating the process of determining parameters in the mathematical model for the non-isometric movement in each subject in accordance with an embodiment of the present invention.

FIG. 3 presents a flowchart illustrating the process of determining parameters in the mathematical model for the non-isometric movement in each subject in accordance with an embodiment of the present invention.

The process starts with determining a stimulator voltage (step 300). Specifically, the stimulator voltage is determined by gradually increasing the FES voltage applied to the muscle until a maximal voluntary contraction (MVC) force is obtained through measurement. The stimulator voltage is then set to a predetermined percentage of the obtained MVC voltage and kept unchanged throughout the reminder of the testing session.

Next, the process determines parameters under isometric conditions (step 302). Note that under the isometric conditions the angular velocity, $\dot{\theta}$, becomes zero. Hence, Eq. (2) becomes:

$$\frac{dF}{dt} = \left[ \begin{array}{c} a(40-\theta)^2 + \\ b(40-\theta) + A_{40} \end{array} \right] \frac{C_N}{K_M + C_N} - \frac{F}{\tau_1 + \tau_2 \frac{C_N}{K_M + C_N}}. \quad (4)$$

Fixed values $\tau_c$=20 ms and $R_0$=2 are used because previously it has been demonstrated that these values are sufficient for human quadriceps muscles under non-fatigue condition. The values $A_{40}$, $\tau_1$, $\tau_2$, $K_M$ are determined first at 40° of knee flexion by fitting Eqs. (1) and (4) to the measured forces produced by stimulating the muscle with a combination of VFT20 and VFT80 trains. While these parameter values are kept fixed, the values of a and b are determined at knee flexion angles of 15°, 65°, and 90° by fitting the measured force responses to the VFT20-VFT80 train combination. The values of a and b are obtained by first determining the value of A from fitting the VFT20-VFT80 force responses at angles of 15°, 65°, and 90°, and then fitting the values of A at the above four angles to the parabolic equation given by $a(40-\theta)^2+b(40-\theta)+A_{40}$.

The process next determines parameters under isovelocity conditions (step 304). Specifically, when the lower leg moves at a constant velocity, the angular acceleration, $\ddot{\theta}$, becomes zero and Eq. (3) can be written as $$F = F_{KC} + F_{M\text{-}Isovel} \cos \theta. \quad (5)$$

Eq. (5) represents the relationship between the muscle force due to stimulation, F, and the force measured by the KinCom dynamometer, $F_{KC}$. Note that $F_M$ in Eq. (3) is replaced by $F_{M\_Isovel}$ to reflect the difference in $F_M$ values during general non-isometric conditions and isovelocity conditions.

More specifically, the process first obtains the value of $F_{M\_Isovel}$ by fitting the function $F_{M\_Isovel} \cos \theta$ to the passive knee extension force data from 90° to 15° of knee flexion at a constant velocity of –200°/s. Next, the so-obtained value of $F_{M\_Isovel}$ is added to $F_{KC}$ to obtain force F. Finally, Eqs. (1) and (2) are fitted to the force F elicited by the VFT20-VFT80 train combination at –200°/s to obtain the value of $V_1$. Noted that in determining $V_1$, parameters a, b, $A_{40}$, $\tau_1$, $\tau_2$ and $K_M$ are kept fixed at values obtained during step 302.

Finally, the process determines parameters under general non-isometric conditions (step 306). Specifically, the process first determines λ for each subject by subtracting the resting value of θ from the vertical angle of 90°. Next, the process determines the values of the ratio L/I and $F_M$ at each of the three loads (0, 4.54 kg, and 9.08 kg) by fitting the model (Eqs. (1)-(3)) to the shortening velocity response to the VFT20 train.

Applying the Mathematical Model

Figure 4:
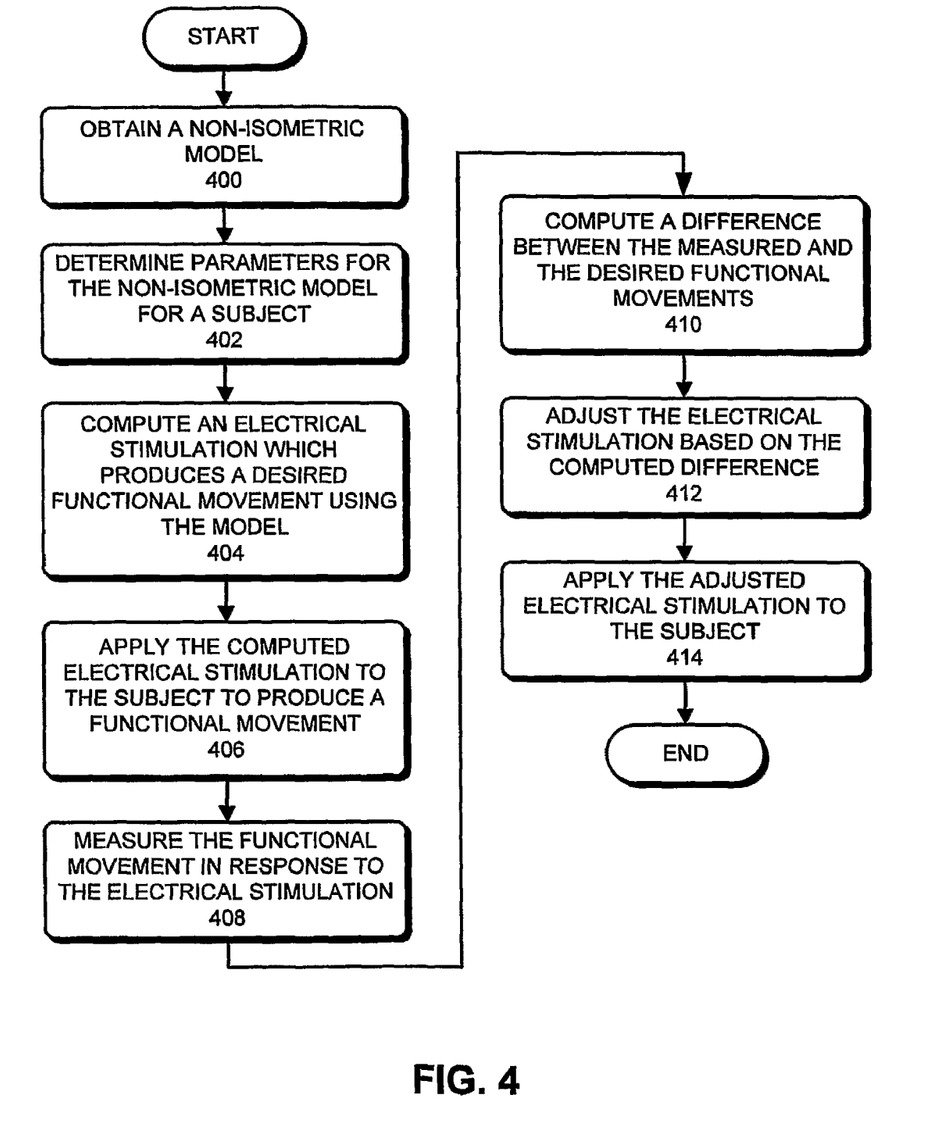
FIG. 4 presents a flowchart illustrating the process of activating a muscle to produce a desired functional movement in a subject through electrical stimulation in accordance with an embodiment of the present invention.

FIG. 4 presents a flowchart illustrating the process of activating a muscle to produce a desired functional movement in a subject through electrical stimulation in accordance with an embodiment of the present invention. In one embodiment of the present invention, the desired functional movement is used to generate an artificial walk function that overcomes foot-dragging for a patient with a foot-drop problem.

The system first obtains a non-isometric model which defines a functional movement associated with the muscle in response to electrical stimulation of the muscle (step 400). In one embodiment of the present invention, the non-isometric model is defined by the above-described Eqs. (1)-(4). Note that the non-isometric model contains multiple parameters that are specific to each of the subject.

Next, the system determines parameters for the non-isometric model empirically for the subject (step 402).

The system then uses the non-isometric model to compute an electrical stimulation which produces a desired functional movement in the subject (step 404). Note that this step can be performed through simulation on a computing device, such as a personal computer.

The system next applies the computed electrical stimulation to the muscle of the subject to produce a functional movement in the subject (step 406).

Next, the system measures the functional movement in the subject in response to the computed electrical stimulation (step 408).

The system then computes a difference between the measured functional movement and the desired functional movement (step 410).

Next, the system uses the computed difference as feedback to adjust the electrical stimulation to facilitate obtaining the desired functional movement in the subject (step 412). If pulse trains are used as the electrical stimulation, adjusting the electrical stimulation then involves changing one of the following in the pulse trains: (1) the IPI; (2) the duration of the pulses; or (3) the amplitude of the pulses. More specifically, adjusting the IPI can involve: (1) adjusting the IPI in a CFT; (2) adjusting multiple IPIs in a VFTs; and (3) adjusting IPIs in a DFTs both within doublets and in-between adjacent doublets.

The system then applies the adjusted electrical stimulation to the muscle (step 414). Note that the system can repeat step 408 to step 414 in a feedback loop until the difference between the measured functional movement and the desired functional movement is sufficiently small, thereby achieving the desired functional movement.

Furthermore, the above-described process, in combination with the non-isometric model which can accurately predict the relationship between frequency and pattern of the electrical stimulation on the functional movements, facilitates choosing an optimal electrical stimulation that both substantially minimizes fatigue in the muscle and produces the desired functional movement in the subject.

The foregoing descriptions of embodiments of the present invention have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

TABLE 1

| Symbol | Unit | Definition |
|---|---|---|
| $C_N$ | — | Variable that represents the normalized concentration of $Ca^{2+}$-troponin complex |
| t | ms | Time since the beginning of the stimulation |
| $t_i$ | ms | Time when the ith pulse is delivered |
| $\tau_c$ | ms | Time constant controlling the rise and decay of $C_N$ |
| $R_i$ | — | Scaling term that accounts for the differences in the degree of activation produced by each pulse relative to the first pulse of the train |
| $R_0$ | — | Mathematical term characterizing the magnitude of enhancement in $C_N$ from the following stimuli |
| F | N | Instantaneous force due to stimulation |
| $A_{40}$ | N/ms | Scaling factor for force at 40° of knee flexion |
| a | N/ms-deg$^2$ | Scaling factor to account for force at each knee flexion angle |
| b | N/ms-deg | Scaling factor to account for force at each knee flexion angle |
| $\theta$ | deg | Knee flexion angle |
| $\dot{\theta}$ | deg/s | Angular velocity of the lower leg |
| $V_1$ | N/deg$^2$ | Scaling factor in the term $G(\theta)$ and is determined at $-200°/s$ |
| $K_m$ | — | Sensitivity of strongly bound cross-bridges to $C_N$ |
| $\tau_1$ | ms | Time constant of force decline at the absence of strongly bound cross-bridges |
| $\tau_2$ | ms | Time constant of force decline due to the extra friction between actin and myosin resulting from the presence of strongly bound cross-bridges |
| $\ddot{\theta}$ | deg/s$^2$ | Angular acceleration of the lower leg |
| L | m | Effective moment arm from the knee joint center of rotation to a point on the shank where all the forces are assumed to act |
| I | kg-m$^2$ | net mass moment of inertia of the lower limb of the leg and the external load wrapped above the ankle joint |
| $F_{M-Isovel}$ | N | Force measured by the KinCom due to the elastic resistance of the knee joint and the weight of the lower limb during iso-velocity conditions |
| $F_M$ | N | Effective force acting on the limb due to elastic resistance of the knee joint and the weight of the lower limb during general non-isometric conditions |
| $F_{KC}$ | N | Experimental force measured by the KinCom dynamometer for isometric and iso-velocity testing |
| $F_{LOAD}$ | N | The external weight wrapped above the ankle joint for non-isometric testing |
| $\lambda$ | deg | Resting angle to ensure that $(F_{LOAD} + M)\cos(\theta + \lambda)$ is zero at the beginning of the stimulation |

What is claimed is:

1. A method for activating a muscle to produce a functional movement in a subject through electrical stimulation, comprising:
    obtaining a non-isometric model which defines a functional movement associated with the muscle in response to electrical stimulation of the muscle, wherein determining parameters for the non-isometric model involves:
        determining a first set of parameters under isometric conditions;
        determining a second set of parameters under isovelocity conditions; and
        determining a third set of parameters under non-isometric conditions;
    using the non-isometric model to compute an electrical stimulation which produces a desired functional movement in the subject; and
    applying the computed electrical stimulation to the muscle to produce the desired functional movement in the subject.

2. The method of claim 1, wherein obtaining the non-isometric model involves determining parameters for the non-isometric model empirically for the subject.

3. The method of claim 1, wherein the non-isometric model defines the relationship between force behaviors in response to an electrical stimulation and movements in response to the electrical stimulation.

4. The method of claim 3, wherein the force behaviors include:
    the force generated by non-isometric contraction of the muscle; and
    the time derivative of the force generated by non-isometric contraction of the muscle.

5. The method of claim 3, wherein the movements include one or more of the following:
- an angular displacement;
- an angular velocity; and
- an angular acceleration.

6. The method of claim 1, wherein an electrical stimulation is a train of pulses, wherein the train of pulses is characterized by:
- interpulse interval (IPI);
- duration of the pulses; and
- amplitude of the pulses.

7. The method of claim 6, wherein the electrical stimulation comprises:
- a constant IPI within the train of pulses; or
- a variable IPI within the train of pulses.

8. The method of claim 6, wherein after applying the computed electrical stimulation to the muscle, the method further comprises:
- measuring a functional movement in the subject in response to the computed electrical stimulation;
- computing a difference between the measured functional movement and the desired functional movement;
- using the computed difference as feedback to adjust the electrical stimulation to facilitate obtaining the desired functional movement in the subject; and
- applying the adjusted electrical stimulation to the muscle.

9. The method of claim 8, wherein adjusting the electrical stimulation involves changing one of the following:
- the IPI;
- the duration of the pulses; or
- the amplitude of the pulses.

10. The method of claim 1, wherein computing the electrical stimulation involves computing an electrical stimulation that substantially minimizes fatigue in the muscle while producing the desired functional movement in the subject.

11. A non-transitory computer-readable storage medium storing instructions that when executed by a computer cause the computer to perform a method for activating a muscle to produce a functional movement in a subject through electrical stimulation, the method comprising:
- obtaining a non-isometric model which defines a functional movement associated with the muscle in response to electrical stimulation of the muscle, wherein determining parameters for the non-isometric model involves:
  - determining a first set of parameters under isometric conditions;
  - determining a second set of parameters under isovelocity conditions; and
  - determining a third set of parameters under non-isometric conditions;
- using the non-isometric model to compute an electrical stimulation which produces a desired functional movement in the subject; and
- applying the computed electrical stimulation to the muscle to produce the desired functional movement in the subject.

12. The computer-readable storage medium of claim 11, wherein obtaining the non-isometric model involves determining parameters for the non-isometric model empirically for the subject.

13. The computer-readable storage medium of claim 11, wherein the non-isometric model defines the relationship between force behaviors in response to an electrical stimulation and movements in response to the electrical stimulation.

14. The computer-readable storage medium of claim 13, wherein the force behaviors include:
- the force generated by non-isometric contraction of the muscle; and
- the time derivative of the force generated by non-isometric contraction of the muscle.

15. The computer-readable storage medium of claim 13, wherein the movements include one or more of the following:
- an angular displacement;
- an angular velocity; and
- an angular acceleration.

16. The computer-readable storage medium of claim 11, wherein an electrical stimulation is a train of pulses, wherein the train of pulses is characterized by:
- interpulse interval (IPI);
- duration of the pulses; and
- amplitude of the pulses.

17. The computer-readable storage medium of claim 16, wherein the electrical stimulation comprises:
- a constant IPI within the train of pulses; or
- a variable IPI within the train of pulses.

18. The computer-readable storage medium of claim 16, wherein after applying the computed electrical stimulation to the muscle, the method further comprises:
- measuring a functional movement in the subject in response to the computed electrical stimulation;
- computing a difference between the measured functional movement and the desired functional movement;
- using the computed difference as feedback to adjust the electrical stimulation to facilitate obtaining the desired functional movement in the subject; and
- applying the adjusted electrical stimulation to the muscle.

19. The computer-readable storage medium of claim 18, wherein adjusting the electrical stimulation involves changing one of the following:
- the IPI;
- the duration of the pulses; or
- the amplitude of the pulses.

20. The computer-readable storage medium of claim 11, wherein computing the electrical stimulation involves computing an electrical stimulation that substantially minimizes fatigue in the muscle while producing the desired functional movement in the subject.

21. A system for activating a muscle to produce a functional movement in a subject through electrical stimulation, comprising:
- a computer;
- an electrical stimulation generator;
- a computing mechanism configured to use a non-isometric model which defines a functional movement associated with the muscle in response to electrical stimulation of the muscle to compute an electrical stimulation which produces a desired functional movement in the subject, wherein determining parameters for the non-isometric model involves:
  - determining a first set of parameters under isometric conditions;
  - determining a second set of parameters under isovelocity conditions; and
  - determining a third set of parameters under non-isometric conditions; and
- an electrical stimulator configured to apply the computed electrical stimulation to the muscle to produce the desired functional movement in the subject.

22. The system of claim 21, further comprising a determination mechanism configured to determine parameters for the non-isometric model empirically for the subject.

23. The system of claim 21, wherein the non-isometric model defines the relationship between force behaviors in response to an electrical stimulation and movements in response to the electrical stimulation.

24. The system of claim 23, wherein the force behaviors include:
the force generated by non-isometric contraction of the muscle; and
the time derivative of the force generated by non-isometric contraction of the muscle.

25. The system of claim 23, wherein the movements include one or more of the following:
an angular displacement;
an angular velocity; and
an angular acceleration.

26. The system of claim 21, wherein an electrical stimulation is a train of pulses, wherein the train of pulses is characterized by:
interpulse interval (IPI);
duration of the pulses; and
amplitude of the pulses.

27. The system of claim 26, wherein the electrical stimulation comprises:
a constant IPI within the train of pulses; or
a variable IPI within the train of pulses.

28. The system of claim 26, further comprising:
a measurement mechanism configured to measure a functional movement in the subject in response to the computed electrical stimulation;
wherein the computing mechanism is configured to compute a difference between the measured functional movement and the desired functional movement;
an adjustment mechanism configured to use the computed difference as feedback to adjust the electrical stimulation to facilitate obtaining the desired functional movement in the subject; and
wherein the electrical stimulator is configured to apply the adjusted electrical stimulation to the muscle.

29. The system of claim 28, wherein the adjustment mechanism is configured to change one of the following:
the IPI;
the duration of the pulses; or
the amplitude of the pulses.

30. The system of claim 21, wherein the computing mechanism is configured to compute an electrical stimulation that substantially minimizes fatigue in the muscle while producing the desired functional movement in the subject.

* * * * *